United States Patent
Idriss et al.

[11] Patent Number: 5,207,666
[45] Date of Patent: May 4, 1993

[54] PASSIVE SHUTTLE METERING DEVICE FOR IMPLANTABLE DRUG DELIVERY SYSTEM

[75] Inventors: Samir F. Idriss, Hyde Park, Mass.; Joshua Makower, Nanuet, N.Y.

[73] Assignee: Infusaid, Inc., Norwood, Mass.

[21] Appl. No.: 752,798

[22] Filed: Aug. 30, 1991

[51] Int. Cl.⁵ .......................................... A61M 31/00
[52] U.S. Cl. ................................ 604/891.1; 604/246; 128/DIG. 12
[58] Field of Search ................ 604/65, 93, 131, 152, 604/246–249, 890.1, 891.1; 128/DIG. 12, DIG. 13; 417/349, 417, 469, 410 R

[56] References Cited

U.S. PATENT DOCUMENTS

| | | | |
|---|---|---|---|
| 4,634,430 | 1/1987 | Polaschegg | 128/DIG. 12 |
| 4,714,462 | 12/1987 | DiDomenico | 604/891.1 |
| 4,838,860 | 6/1989 | Groshong et al. | 128/DIG. 12 |
| 4,838,887 | 6/1989 | Idriss | 604/891.1 |
| 4,931,050 | 6/1990 | Idriss | 128/DIG. 12 |
| 5,109,850 | 5/1992 | Blanco et al. | 604/890.1 |

Primary Examiner—C. Fred Rosenbaum
Assistant Examiner—Manuel Mendez
Attorney, Agent, or Firm—Sughrue, Mion, Zinn, Macpeak & Seas

[57] ABSTRACT

A fluid metering device useful in implantable drug delivery systems is coupled between a pressurized fluid source and an outlet conduit to provide discrete flow pulses at a predetermined rate. The metering device consists of a first movable member constrained within a housing and a second movable member retained in a cavity by the first. Alternate positioning of the first member simultaneously fills and empties the cavity in which the second resides, discharging fluid through the conduit. The first movable member can be a planar slider, an axially translatable cylinder or a rotatable cylinder. The second movable member may be a flat shuttle, a sliding bar or a diaphragm.

23 Claims, 8 Drawing Sheets

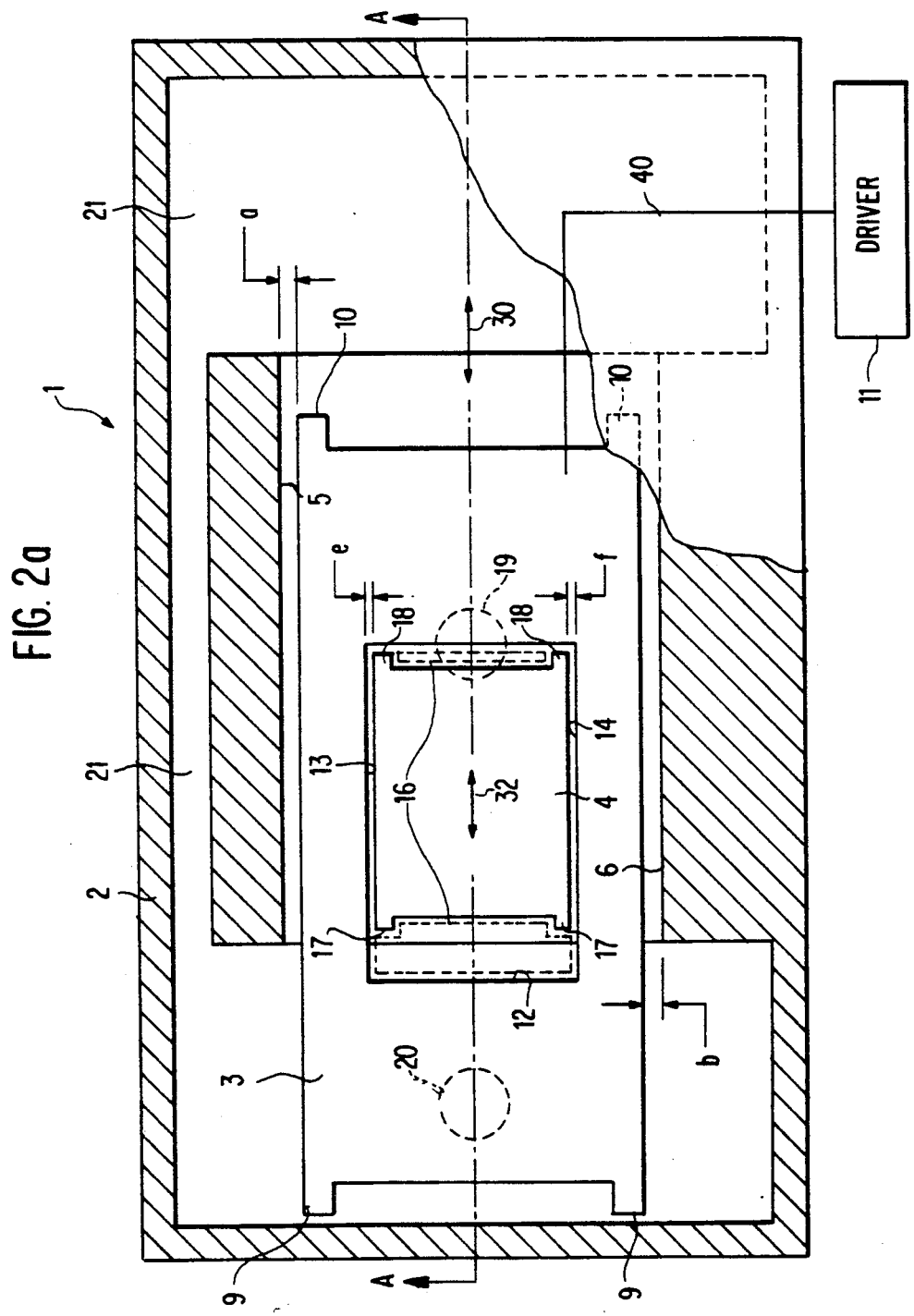

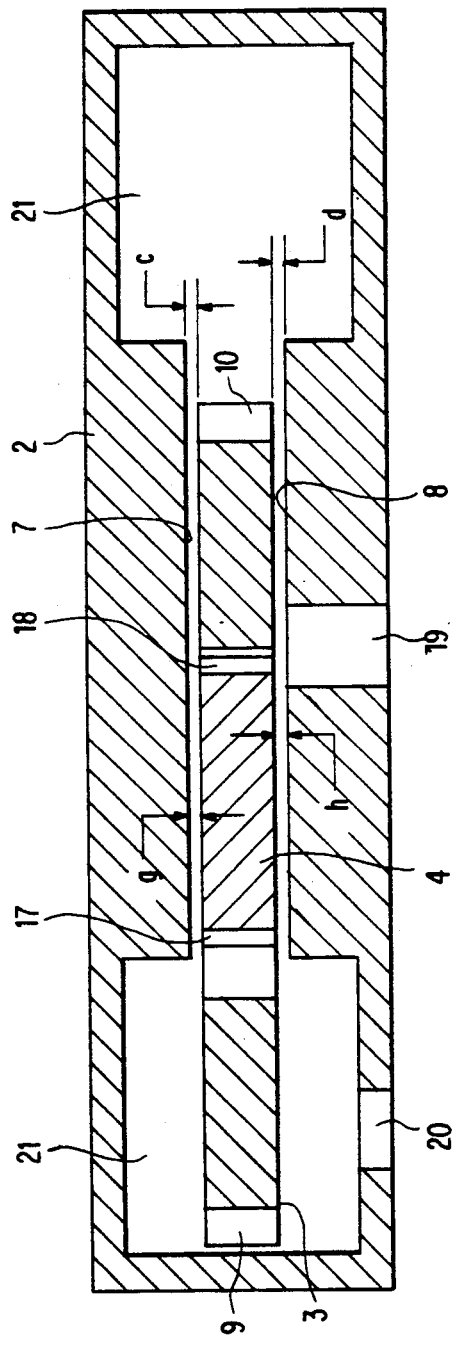
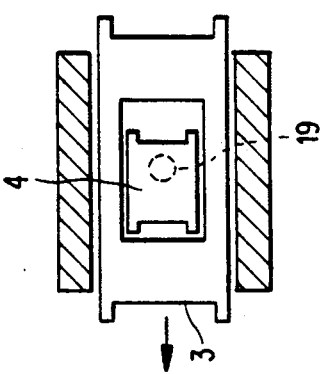
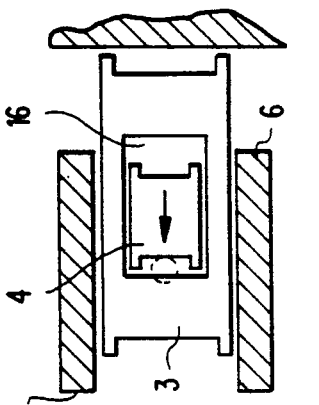
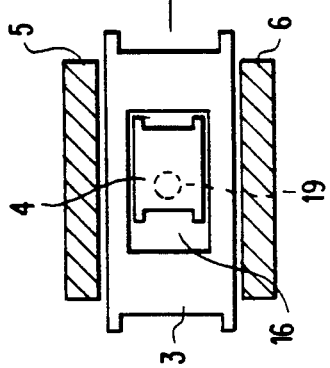
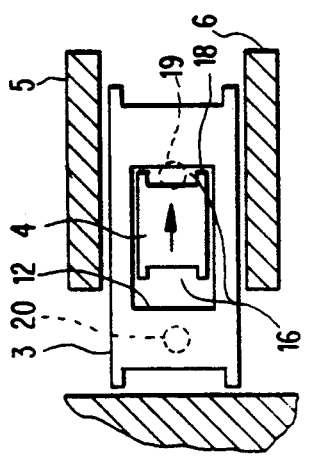

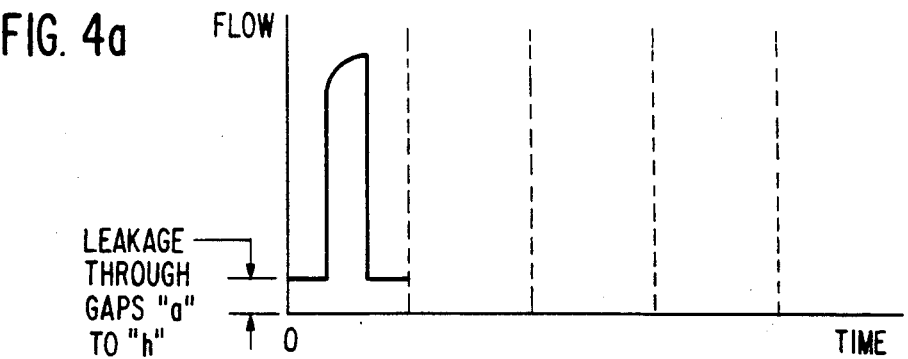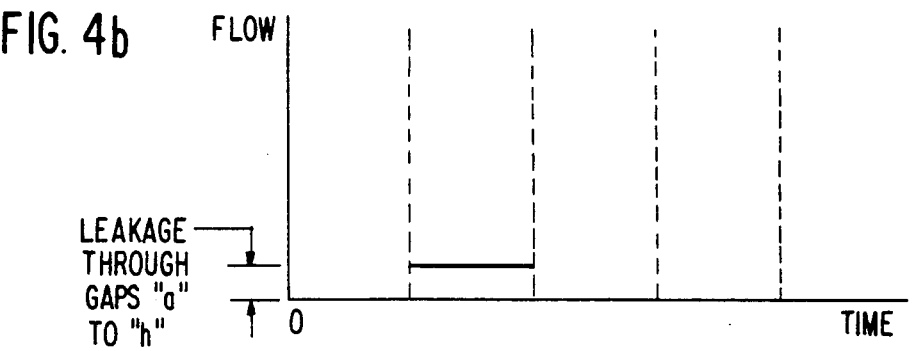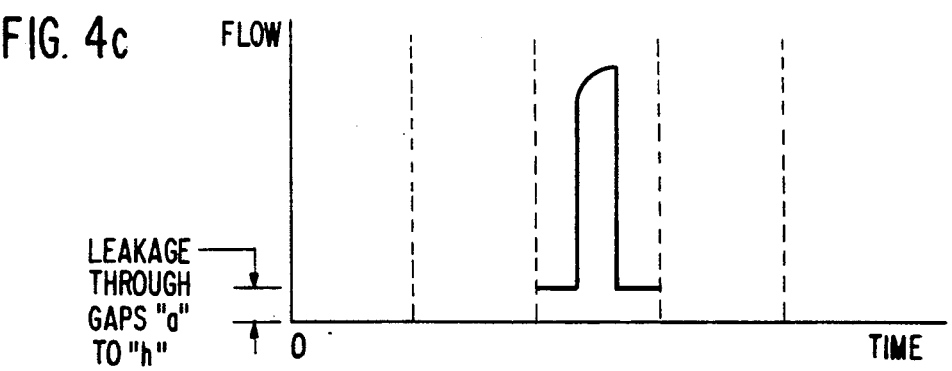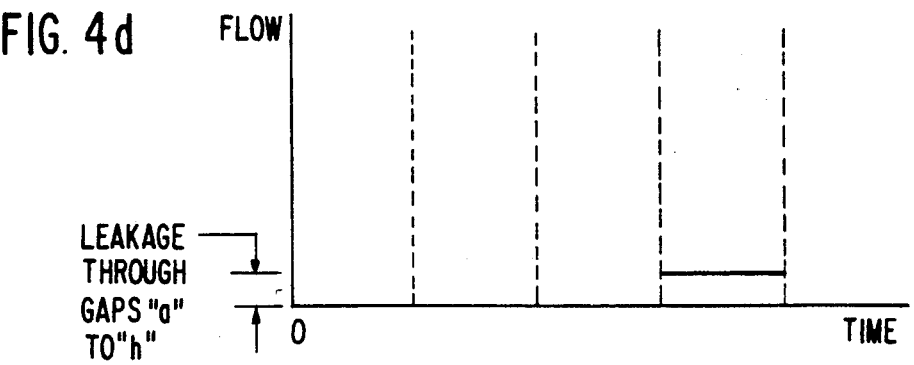

PASSIVE SHUTTLE METERING DEVICE FOR IMPLANTABLE DRUG DELIVERY SYSTEM

BACKGROUND OF THE INVENTION

This invention is directed to a metering device for use in implantable drug delivery systems. In particular, this invention is a fluid metering component that is inherently fail-safe yet utilizing very low operating power.

Implantable infusion systems are used in a number of medical applications. Typical are the INFUSAID Model 100 and Model 400 devices. Those systems are based on the technology embodied in U.S. Pat. No. 3,731,681, which employs a bellows drug reservoir that is driven by the use of a propellent in the form of a fluid liquid/vapor component such as Freon 11 (DuPont tradename). The liquid/vapor equilibrium is employed to pressurize the bellows drug reservoir at a positive pressure. These systems serially connect the drug containing reservoir to a capillary flow channel that meters the drug via viscous dissipation. The capillary flow employs a tube as a catheter at the exit, the situs of drug delivery. For a specific drug concentration, the flow rate is maintained at a relatively constant level depending upon the pressure difference between the reservoir and the catheter exit.

In more contemporary applications there is a necessity for the patient to vary the pump flow rate on a routine basis between pump refills. Examples of such therapies are: the continuous administration of insulin to counter diabetes, the bolusing of morphine for patient controlled analgesia and the alternate delivery and rest cycles used in chemotherapy of the liver. To provide such programmability, a number of different metering devices have been combined with positive pressure reservoirs. An example is the two-position solenoid used in conjunction with a volume accumulator as disclosed in U.S. Pat. No. 4,221,219. The system of the '219 patent allows different drug flows as a function of solenoid position by gating fluid into and out of the accumulator.

A self regulating flow restrictor having an adjustable set point is disclosed in U.S. Pat. No. 4,447,224. A system employing a leaking check valve in combination with a high pressure solenoid pump is disclosed in U.S. Pat. No. 4,714,462. A valve/accumulator/valve assembly employing a pressurized accumulator is disclosed in U.S. Pat. No. 4,838,887.

All of these prior art systems employ a positive pressure reservoir. That is, the reservoir is pressurized at a level higher than that of the outlet. This system configuration has both advantages and disadvantages as a function of the type of device used to meter the output. A positive pressure reservoir, for example, is advantageous in that it prevents large scale outgassing of drug solutions. This precludes the formation of air bubbles which would potentially alter the metering system dosage rate or provide danger to the patient by direct infusion of air. Additionally, the use of a positive pressure reservoir will significantly reduce the amount of energy required to meter flow, because less energy is needed in the controlled gating of a volume of fluid under pressure than in the active pumping of the same volume of fluid at the same pressure. However, inherent in the use of positive pressure reservoir technology is the potential for catastrophic flow in the event of a metering system failure. Unrestrained leak paths can potentially permit uncontrolled discharge of the reservoir contents. This may result in injury or death to the patient.

The valve/accumulator/valve system as typified in U.S. Pat. No. 4,838,887 has been particularly successful in achieving high accuracy of dosage delivery, relative immunity to entrapped air, a wide programmability range and safe operation. Moreover, this configuration requires moderate operating energies. This results in a reasonably long implant life for the system. However, inherently, these devices have a high initial cost associated with the sophisticated design, manufacture and assembly of discrete valve and accumulator components. These cost implications may prevent this pump configuration from achieving wide spread and common use.

An important aspect of the valve/accumulator/valve design is that the use of two valving elements provides the necessary redundancy to increase pump safety. The independent nature of the valves allows a mutually exclusive electronic "lock-out" in the event of a single point valve failure.

These first and second generation implantable pump configurations provided a baseline upon which the technology could be assessed and discrete improvements considered. There still exists an important need for a system which would have a lower energy requirement, thus permitting longer times between explant for replacement. Moreover, a follow-on design should have a smaller size than the original devices to permit implantation in a variety of different sites and a much lower cost of manufacture to increase the number of patients who could purchase the device and benefit from its use. Although the reliability, of the valve/accumulator/valve technology in particular has been shown to be exceptional, the use of two independent valves is not failsafe from a mechanical standpoint and could permit undetectable leakage modes. Therefore, new technology should be failsafe from a mechanical standpoint, for instance, providing for mutual exclusivity of valve position.

SUMMARY OF THE INVENTION

Given the state of the art in implantable pump technology, it is an object of this invention to provide a metering device which employs a simplified active driving member to regulate discrete quantities of infusate without the use of independently controlled valves or a pressurized volume accumulator.

Yet another object of this invention is to provide for a programmable, pulsed flowrate profile which can be altered to provide flowrates ranging from low-level continuous basal infusion to high-level bolus dosing.

Still another object of this invention is to provide a device which improves patient safety by eliminating potentially catastrophic leakage modes through the use of internal sealing dependent solely on the geometries of rigid elements or elastic members in fixed contact plus the mutual exclusivity of flow control positions.

A further object of this invention is to provide an implantable metering system that significantly reduces costs by integrating valve and accumulator components and simplifying the number and type of parts.

A still further object of this invention is to provide a volume gating system which reduces energy consumption yet permits device operation that is independent of temperature, drug viscosity, reservoir pressure and pump exit pressure.

These and other objects of this invention are achieved in an implantable delivery system which employs a passive shuttle metering device. The shuttle metering device accurately provides a dose rate in discrete quantities from a positively pressurized drug reservoir. The shuttle mechanism employs an active moving element and a passive shuttle element. It is inherently failsafe without any catastrophic leak modes due to jamming of components or particulate contamination.

This invention will be described in greater detail by referring to the attached drawings and the description of the preferred embodiments which follow.

BRIEF DESCRIPTION OF THE DRAWINGS

FIGS. 2a and 2b are a plan and sectional view, respectively, of a first preferred embodiment of this invention;

FIGS. 3a–3d illustrate, schematically, the operation of the shuttle mechanism in accordance with the first embodiment;

FIGS. 4a–4d are flow versus time graphs illustrating the flow outputs of the infusion system with the shuttle in the corresponding positions of FIGS. 3a–3d;

DESCRIPTION OF THE PREFERRED EMBODIMENTS

Figure 1:
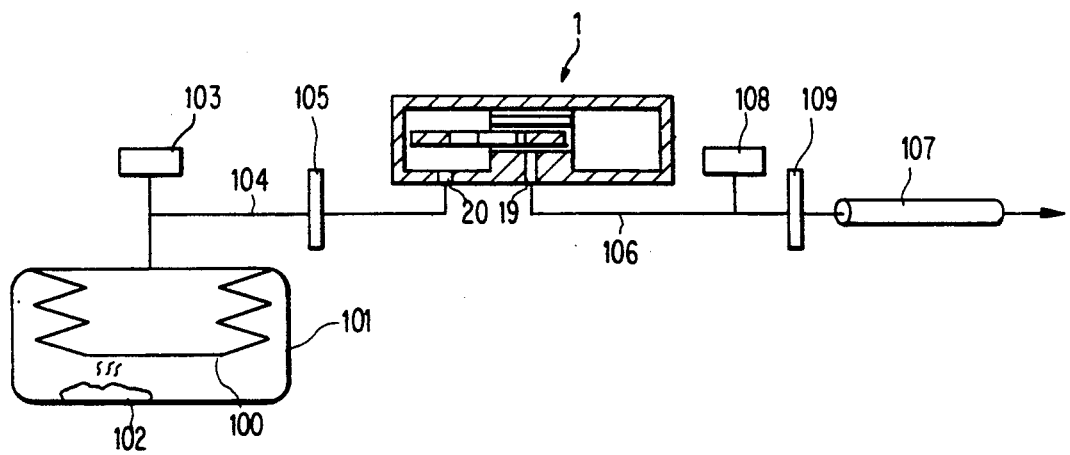
FIG. 1 is a schematic drawing illustrating the essential components of an implantable drug delivery system using this invention.

Referring now to FIG. 1, a schematic illustration of the implantable system of this invention is depicted. A flexible reservoir 100, typically a bellows, is housed in a container 101, to enclose charging fluid 102, typically Freon. The charging fluid 102 provides a stable vapor/liquid pressure to bias the reservoir 100 at a relatively constant pressure irrespective of volume.

A refill septum 103 provides access to the reservoir 100 for purposes of refilling the reservoir with infusate. Conduit 104 provides a tap and outlet from reservoir 100 to the outlet catheter 107. Interposed between the reservoir 100 and catheter 107 is a bacteria/air filter 105, a passive shuttle metering device 1, flow conduit 106, access septum 108, and particulate filter 109. The metering device 1 has an outlet 19 and inlet 20. The inlet 20 is coupled to the conduit 104 downstream of the bacteria/air filter 105, while the outlet 19 is positioned in the flow conduit 106 upstream of the access port 108 and the particle filter 109.

The schematic system in FIG. 1 is for purposes of illustration. A number of modifications may be used in actual practice. For example, while the reservoir 100 is shown as typical of the first generation Model 100 and Model 400 systems, it is apparent that any source under positive pressure can be used. That is, the bellows-Freon example is only one of a variety of positive pressure infusate sources. Moreover, while the filters 105 and 109 are relatively customary in these implantable systems, they are not mandatory. Similarly, the access port 108, while offering unique advantages is not a mandatory part of the system, and even the refill septum 103 can be eliminated from a pump intended for one-time use.

Referring now to FIGS. 2a and 2b, the passive shuttle metering device 1 of this invention will be described in greater detail. The device is contained in a housing 2 having therein a planar slider 3 and a shuttle element 4. As illustrated by the arrow 30, the slider 3 moves within the housing 2 back and forth on guides 5 and 6. Tolerance gaps "a" and "b" are established between the sides of the slider 3 and the guides 5 and 6. The tolerance gaps "a" and "b" thus tend to establish the limits for longitudinal skewing of the slider 3 as it traverses in the directions of the arrow 30. As illustrated in FIG. 2b, vertical tolerance limits are also established by gaps "c" and "d" relative to top and bottom planar bearing surfaces 7 and 8. Consequently, by having lateral guides 5 and 6 and vertical guides 7 and 8, the slider 3 is constrained for essentially linear movement in the directions of the arrow 30.

Two pairs of mechanical stops 9 and 10 define the limits of motion of the slider 3 relative to the sides of the housing 2. The slider is driven by a driver 11 (shown in schematic form) through driving linkage 40. The driver is employed only to change the position of the slider and may be any direct, remote, manual or automatic device used to manipulate the position of the slider 3. Various alternatives for the driver 11 will be discussed herein.

As illustrated in FIG. 2a, a cutout 12 is formed within the body of the slider 3. The cutout retains the shuttle member 4. Movement of the shuttle 4 in the direction of the arrow 32 is fixed within the slider by intimate contact at edge bearing surfaces 13 and 14 in the horizontal plane and again between surfaces 7 and 8 in the vertical plane. These establish tolerance gaps "e" and "f" horizontally and tolerance gaps "g" and "h" vertically. As illustrated in FIGS. 2a and 2b, the cutout 12 has a length greater than that of the shuttle 4. A constant volume space 16 is defined by the dashed lines in FIG. 2a, representing the difference between the spatial volume of the cutout 12 and the spatial volume of the shuttle 4. This volume 16 is variably distributed depending upon the relative location of the shuttle 4 to the slider 3. For instance, a larger portion of the volume space 16 exists to the left of the shuttle 4, as depicted in FIG. 2a, than to the right of the shuttle 4. Given that the shuttle 4 is housed within the cutout 12, the total volume of the space 16 remains constant irrespective of the position of the shuttle. Thus, as the shuttle moves within the cutout 12, the volume components may shift to the right or left but the total volume space 16 remains constant.

Therefore, in accordance with this invention, the unswept volume, that is the space which is not positively cleared or displaced by the movement of the shuttle 4, can be designed very small with respect to the volume that is displaced by the shuttle. Thus, any air which is accidentally trapped between the shuttle 4 and the slider 3 will be minimal and will not significantly increase the pulse volume of the metering device.

As illustrated in FIG. 2a, end tabs 17 and 18 functioning as end stops limit the travel of the shuttle 4 within the cutout 12 such that fluid can flow between respective ends of the shuttle 4 and slider 3 as the shuttle ends are positioned in communication with inlet 20 or the outlet 19. For example, the righthand end of shuttle 4 is illustrated as positioned over outlet 19 and the lefthand end exposed to fluid cavity 21 which is in fluid communication with inlet 20. By providing the tabs 17 and 18, flow gaps are made large enough between shuttle 4 and the walls of the cutout 12 so that rapid filling and discharging of the volume space 16 can be accomplished with unhindered movement of the shuttle 4.

Fluid outlet port 19 is positioned in the housing 2 to permit complete discharge of the portion of volume space 16 that resides over the outlet. Inlet port 20 is located within housing 2 to permit simultaneous communication with the remainder of volume space 16 via the internal housing cavity 21.

In operation, the passive shuttle metering device 1 is attached to the reservoir 100 where it receives input via inlet 20. By movement of the slider 3 and the corresponding response of passive shuttle 4, a discrete, metered amount is delivered to the outlet 19. A stepwise description of the operation of this device is illustrated in FIGS. 3a-3d and FIGS. 4a-4d.

Referring now to FIGS. 3a and 4a, a stepwise operation of the metering device with its corresponding flow output (as observed at the exit of the discharge catheter 107) is depicted. With the slider 3 positioned as illustrated in FIG. 3a, hydraulic pressure against the left face of the shuttle 4 resulting from the high pressure inlet 20 forces the shuttle 4 against the fluid on the right side of the volume space 16 which is in communication with the low pressure outlet 19. The slider 3 is latched to the left by means of the driver 11 (not shown in FIGS. 3a-3d) while the shuttle 4 moves to the right in response to the pressure differential between the inlet and outlet as shown by the arrow. Fluid in the right side of the volume space 16 is thus exhausted through the outlet port 19 as the shuttle 4 moves from left to right within the cutout 12. Simultaneous with the discharge of the righthand side of volume space 16, the lefthand portion of the volume space 16 is filled. Consequently, the pressure difference across the shuttle 4 that causes it to move from its left-most position to its right-most position within the slider 3, forces a pulse of fluid volume from the metering device 1 through the flow conduit 106 and out of the catheter 107 (see FIG. 1). In FIG. 3a, the shuttle is shown at the completion of its right-hand movement with limit tabs 18 contacting the righthand wall of the cutout 12.

The resultant flowrate pulse with respect to time is illustrated in FIG. 4a. Given the fixed geometries of the cutout 12 and shuttle 4, the magnitude of this flowrate pulse is repeatable and fixed, being defined by the travel of the shuttle 4 as it moves within cutout 12. As noted in FIG. 4a, a small leakage rate exists through the device as defined by the flow from inlet 20 to outlet 19 through clearance gaps a,b,c,d,e,f,g and h. By judicious choice of tolerances for these gaps, the leakage can be controlled to a significantly small value with respect to the operating output of the device.

FIGS. 3b and 4b now illustrate a second, transitory position of the slider 3 and shuttle 4 as the slider 3 is being repositioned towards the right by driver 11. When a second flow pulse is required, the slider 3 is moved to the right as illustrated by the arrow in FIG. 3b. The shuttle 4 is maintained stationary in the slider 3 by fluid pressure; as the slider 3 is moved, fluid in the lefthand side of the volume space 16 which was previously exposed to high pressure from the inlet 20, now moves toward the low pressure outlet port 19 while simultaneously exposing the righthand face of volume space 16 to high pressure fluid in communication with the inlet 20 via cavity 21 (see FIGS. 2a and 2b). During this transition, flow from the catheter 107 is at the background leakage rate defined through gaps "a" to "h" as graphed in FIG. 4b.

The mechanical work supplied to the driver 11 to move the slider 3 equals the viscous fluid loss encountered in flow gaps "a" to "d" and "g" to "h" due to fluid shear during the movement. Depending on the viscosity of the fluid and the rate at which the slider 3 is moved, this loss may be minimized. When combined with the work needed to accelerate the slider 3, fluid volume 16 and shuttle 4, a totality of the energy required by the driver 11 to operate the metering device 1 during transition can be determined.

Referring now to FIG. 3c, a third position is illustrated schematically similar to that of FIG. 3a. The slider 3 has now reached the far righthand limit of its travel, allowing fluid in the lefthand side of the volume space 16 to communicate with the low pressure of outlet port 19 and the fluid in the righthand face of the shuttle 4 to be exposed to reservoir pressure. Thus, an imbalance across the shuttle 4 from its righthand face to lefthand face causes movement toward the left as illustrated by the arrow in FIG. 3c. Opposite to the direction of FIG. 3a, the new shuttle movement displaces the lefthand contents of the volume 16 through the outlet port 19 while at the same time refilling the righthand volume space. The resultant fluid discharge pulse, illustrated in FIG. 4c, is equivalent to that in FIG. 4a albeit displaced in time. As in FIG. 4a, a constant leakage rate is present upon which the pulse is superimposed.

FIG. 3d illustrates a fourth, transitional position of the slider 3 and shuttle 4. When an additional fluid pulse is required, the slider 3 is driven from its FIG. 3c position in the direction of the arrow towards the FIG. 3a orientation. This transition is functionally identical to that described in FIG. 3b. During the transition, the volume flowrate is given by the leakage flow illustrated in FIG. 4d.

Thus, as illustrated in FIGS. 3a-3d, in one complete cycle of the slider 3, two identical fluid volume pulses are discharged at a pressure differential equivalent to the difference between the pressures in the drug reservoir 100 and delivery catheter 107. The cycling of the slider 3 at a specific rate determines the output of the passive shuttle metering device 1.

As shown by FIGS. 3a-3d, any jamming or clogging of the slider 3 and/or shuttle 4 in any position will not create a catastrophic increase in flowrate. In fact, the flowrate resulting from a jammed device will only be the leakage flow through the gaps "a" to "h" as previously discussed relative to FIG. 4. This should be compared to the valve/accumulator/valve system in which a stuck-open valve can cause a significant flowrate increase and lead to a catastrophic overdose should both valves jam open. Moreover, depending on the choice of material for the housing 2, slider 3 and shuttle 4, surface tension effects may be used to enhance air entrapment in tolerance gaps "a" to "h". The air will reduce the high shear forces during slider 3 motion and therefore, the overall energy and time for repositioning. It will also reduce the leakage through the device by creating a vapor seal. Alternatively, permanent magnets combined with ferromagnetic fluids could be employed to seal the gaps.

Figure 5A:
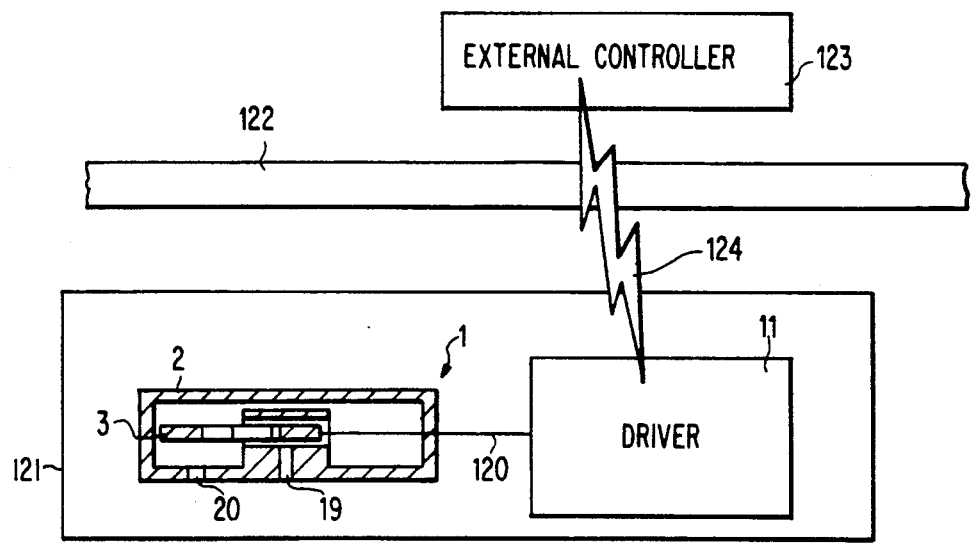
FIG. 5a is a schematic drawing illustrating the generalized control and driving scheme of this invention as implanted in a living body.

Referring now to FIG. 5a, the first preferred embodiment of the passive shuttle metering system 1 is incorporated schematically within an implantable infusion system in an effort to describe the interrelationship between various control and actuation means. In FIG. 5a, the metering device 1 is depicted as residing within a pump housing 121. This system has been implanted under the skin line 122. It will therefore be understood that the housing 121 contains those infusion system elements described in FIG. 1. The driver 11 is connected to the slider 3 via linkage 40. This linkage is a technique by which actuation of the driver 11 provides the translation and movement of the slider 3. The linkage 40 can therefore be a mechanical linkage physically coupling the driver 11 to the slider 3. It may also be an electrostatic, magnetic, thermal or fluid linkage. The driver 11 can be a motor, a magnet, a spring element, solenoid, shape memory alloy, compressible fluid or heating element, etc. The driver 11 may be programmable or fixed with a preset flow regime. Implementation of any of these driver and linkage concepts would be appreciated by one of working skill as requiring a matching of the driver element 11 to the appropriate driver linkage 40 and is within the scope of known technology once the driver has been selected for a particular application.

A generalized external controller 123 is illustrated in FIG. 5a as being in communication with the driver 11 via linkage 124 across skin surface 122. The communication link 124 is used to either transmit command information to the driver 11 or transmit power by which the driver 11 acts as a transducer to move the slider 3 via linkage 40. Thus, communication through the linkage shown schematically as element 124, may be electrical, magnetic, electromagnetic, mechanical, hydraulic, thermal or even optical. An example of a simple external controller 123 could be a plastic button to exert pressure on the skin line 122 under which a stiff, elastic membrane is bonded to the slider 3. The transmission of pressure from the button through the skin to the membrane would move the slider 3; whereby upon release of the button, the elasticity of the membrane would restore the slider 3 to its original position. Therefore, each depression of the button on the skin would result in the discharge of two flow pulses. Likewise, a more sophisticated external controller 123 could be a microprocessor-based hand held unit which could provide information to an implanted telemetry coil via a radio frequency link. An implanted microprocessor and power supply would deliver intermittent energy to a motor that would reciprocate the slider 3 via a shaft through a fluid seal. Both of these schemes are reasonably within the scope of implantable pump technology.

The driver 11 and linkage 40 are shown schematically as separate elements. It will be appreciated however that they may be the same element. For example, the external controller 123, if microprocessor based, could contain all of the programmed information to directly control, in real time, actions of slider 3. A permanent magnet could be bonded to the slider 3 and controlled by a second permanent magnet external to the skin line 122. The position of the external magnet could, in turn, be controlled by a programmable linear actuator. In such a set up, the internal permanent magnet with its bonding agent is both the driver 11 and the linkage 40. The external permanent magnet and the programmable actuator would constitute the controller 123 and the field generated by the magnet would provide the communication link 124.

Figure 5B:
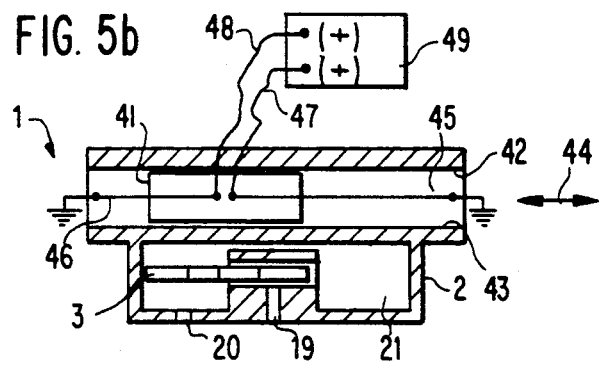
FIG. 5b depicts a preferred configuration for the metering device driver.

As an example of a preferred embodiment, FIG. 5b illustrates a magnetic driver 11 and linkage 40 actuated by shape memory alloy wires. For example, the slider 3 is manufactured from a corrosion resistant, ferromagnetic alloy and a movable permanent magnet element 41 is constrained by bearing surfaces 42 and 43 which are constructed as part of slider housing 2. The translational axis of motion of the magnet 41 is shown by the double headed arrow 44, indicating a motion parallel to that of the slider 3. It is apparent that the attraction of the ferromagnetic slider 3 to the magnet element 41 will link the components together such that when the magnet 41 is moved to the right, the slider 3 moves to right and visa versa. This relationship allows the motion of the slider 3 to be controlled in a manner that doesn't violate the fluid hermeticity of the passive shuttle metering device 1.

Considering again FIG. 5b, the position of the magnet 41 is controlled by two nickel-titanium shape memory alloy (SMA) actuator wires 45 and 46 which are mechanically attached to the center of the magnet 41 but electrically insulated from each other and from the magnet body. To the actuator wires 45 and 46 are respectively mounted electrical leads 47 and 48 which are in turn connected to electronic pulsing module 49. The actuator wires 45 and 46 are also attached at their outer ends, both mechanically and electrically, to housing 2 as shown in FIG. 5b.

Activation of electrical leads 47 or 48 via pulsing module 49 causes current to flow in SMA wires 45 or 46 respectively; this results in internal heating and axial contraction of the wire. In the case of activation of memory wire 45, the contraction will pull the magnet 41 to the right, or in the case of memory wire 46, to the left. The repeated cycling of wires 45 and 46 via leads 47 and 48 is used to reciprocate the position of magnet 41 which will in turn drive slider 3 in a back and forth motion. This will result in an output stream of fluid pulses from metering device 1 and hence, a controlled pump infusion rate. The use of electrically stimulated shape memory alloy wires as simple low cost, high force actuators is well known; their theory of operation will not be described herein. Reference can be made to technical guides such as "Using Shape Memory Alloys", Darel Hodgson, Ph.D., Shape Memory Applications, Inc., Sunnyvale, Calif., 1988, for additional details on these elements.

Comparing now the elements of FIG. 5a to the infusion control system of FIG. 5b: the magnet 41, bearing surfaces 42 and 43, actuators 45 and 46, leads 47 and 48, and programmable power source 49 all taken together correspond to the driver element 11, while the magnetic attraction between the ferromagnetic slider 3 and the permanent magnet 41 constitutes the connecting link 40. FIG. 5b then represents a simple, specific embodiment of driver 11 and connecting link 40 which requires low power consumption, a small number of parts and corresponds to a low cost of manufacture.

Figure 6A:
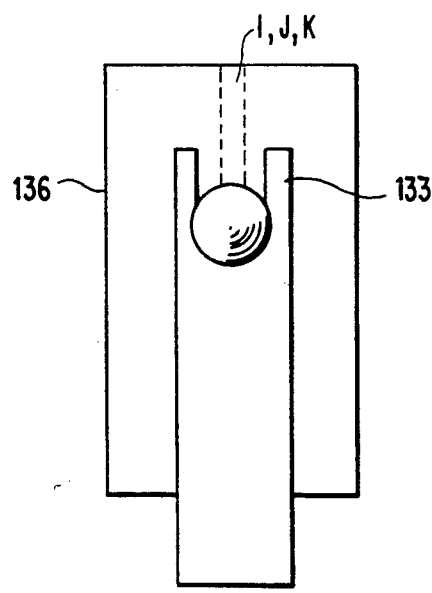
FIGS. 6a and 6b illustrate a second preferred embodiment of this invention utilizing a cylindrical linear system.
Figure 6B:
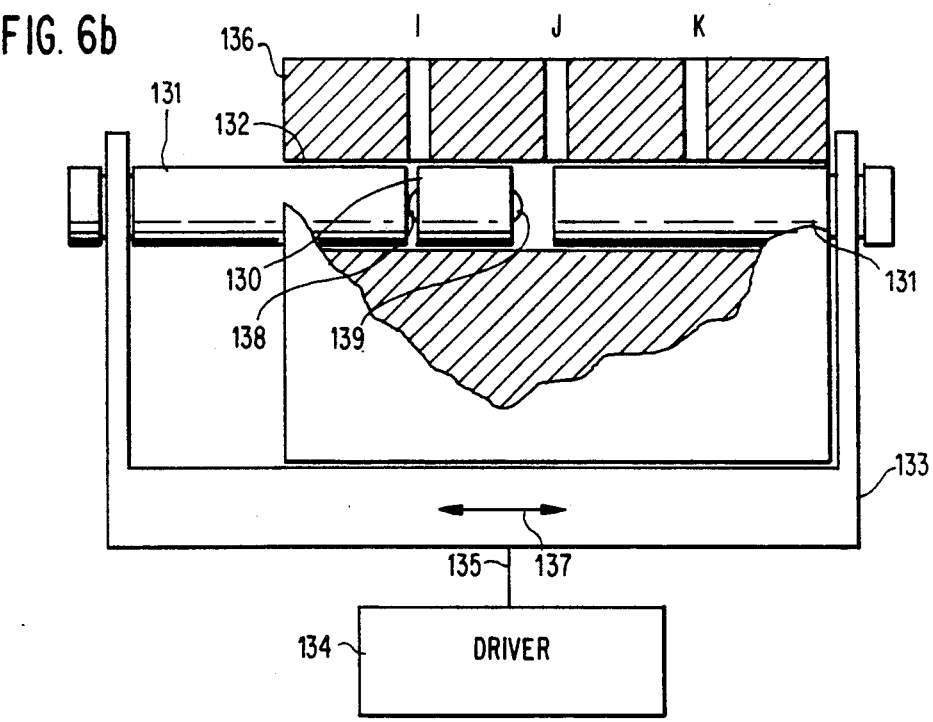

Referring now to FIGS. 6a and 6b, a second preferred embodiment of the passive shuttle invention is depicted. FIGS. 6a and 6b illustrate the use of a cylindrical linear system in which the shuttle member 130 is cylindrical and the slider 131 is also a cylindrical element co-axial with the shuttle. In this embodiment the high pressure inlet has been relocated to the central position, shown in the cut away front view FIG. 6b as channel "J"; it is positioned in the center of two low pressure outlets "I" and "K".

The cylindrical shuttle 130 is constrained by two halves of the cylindrical slider 131 within a close-fitting cylindrical bore 132 in the housing 136. The position of the cylindrical slider 131 is maintained by a yoke 133, the movement of which is controlled by driver element 134 through linkage 135 as illustrated by the two-sided arrow 137. As in the case of the first preferred embodiment of FIGS. 1–5b, the manner in which energy transfer occurs through linkage 135 is a matter of choice as is the nature of the driver 134. Limit stops 138 and 139 are used to prevent intimate contact of the faces of the shuttle 130 with the slider 131 so that the response of the shuttle 130 in separating from the slider 131 will be rapid during its reciprocal movement.

In FIG. 6b it should be noted that the pressures in the channels "I", "J", and "K" are reversed from high to low with respect to FIG. 1. In this second preferred embodiment as in all embodiments, the pressure sense in the inlet and outlet channels may be switched from low to high and visa-versa without affecting the overall operating principles of the invention. Design choice for a particular application will dictate the sense of the flow channels. In all other respects, the operation of this embodiment is identical to the device of FIGS. 2a and 2b and therefore will not be described in further detail.

Figure 7A:
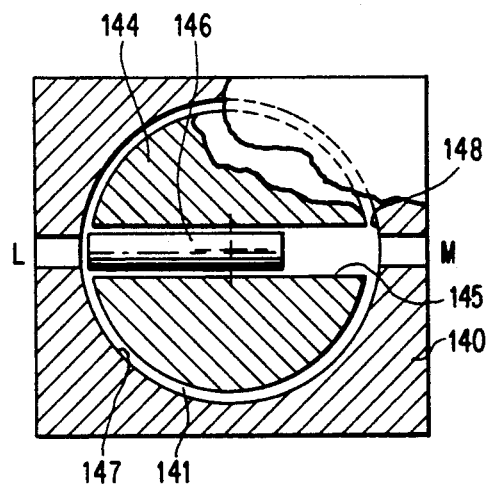
FIGS. 7a and 7b illustrate a third preferred embodiment of this invention employing a cylindrical rotating mechanism.
Figure 7B:
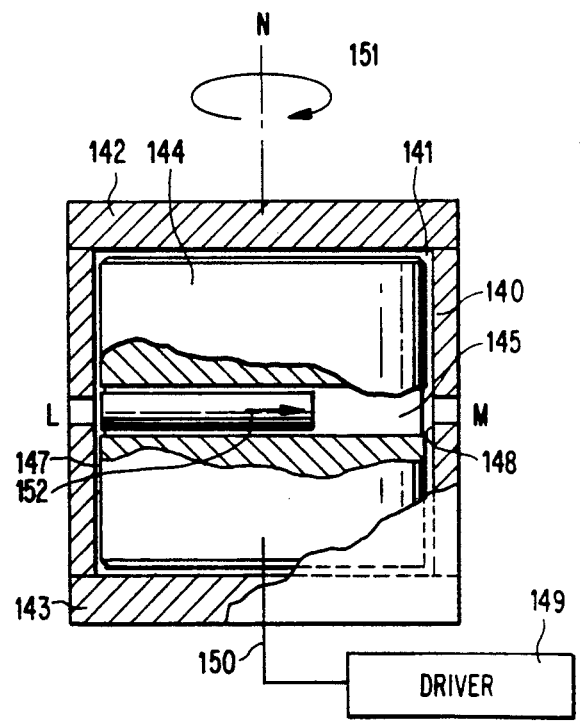

FIGS. 7a and 7b illustrate a third preferred embodiment of this invention. In this embodiment the slider is a rotary element with a cylindrical shuttle contained therein. More specifically, housing 140 has a vertical cylindrical bore 141 enclosed by a top cap 142 and bottom cap 143. Such is illustrated in the cut away side-view FIG. 7b. A cylindrical rotary slider 144 is free to rotate in the cylindrical bore 141 about an axis of rotation "N". High pressure channel "L" transmits fluid into the shuttle passage 145 toward the low pressure channel "M". Referring to FIG. 7a, the cutaway top view, the high pressure side of the shuttle passage 145 fills with fluid from channel L while fluid in the low pressure side is simultaneously discharged through channel M due to the motivation of the pressure differential between the flow channels L and M across the faces of the shuttle 146; the effect is to force the shuttle element 146 to move to the right. Motion of the cylindrical shuttle 146 is limited by left-hand and right-hand mechanical stops 147 and 148, which are simply parts of the cylinder bore 141 as illustrated in FIGS. 7a and 7b. The geometrically constrained movement of the shuttle 146 provides an accurate and repeatable metering of fluid volume as the cylindrical slider 144 is rotated about the axis N as described below.

In operation, when a new pulse is to be delivered, rotary slider 144 turns about the axis N by action of the driver 149 via the energy linkage 150. Following a 180° movement of rotary slider 144 in the direction of the curved arrow 151, the position of the cylindrical shuttle changes from its normal right-hand resting position near channel "M" to a left-hand position near channel "L" (this is the position shown in FIGS. 7a and 7b i.e., just after rotation of the slider 144 and just before the shuttle 146 responds to the pressure difference between the channels L and M). The new pressure differential across the faces of the cylindrical shuttle 146 again causes movement of the cylindrical shuttle 146 in the shuttle passage 145 from left to right as shown by the arrow 152. This movement allows filling of the left side of the shuttle passage 145 with high pressure fluid from channel L and simultaneous expulsion of a controlled fluid volume from the righthand side through low pressure channel M. Repeated rotation of the slider 144 will cause repeated discharging of discrete fluid volumes as the shuttle 146 is alternately exposed to the high/low pressure differential.

It will be appreciated by those of working skill that the same defined pulse volume can be made to exist in this embodiment as in the other embodiments. Similarly, clearance gaps are established as in the first embodiment between shuttle passage 145 and cylindrical shuttle 146, rotary slider 144 and cylindrical bore 141, top cap 142 and rotary slider 144, and bottom cap 143 and rotary slider 144. By judicious choice of tolerances, these gaps can be designed to minimize any fluid leakage during the period between volume pulses. In all other respects, the operation of this system is identical to that of the first embodiment and the flow waveforms illustrated in FIGS. 4a–4d.

Figure 8A:
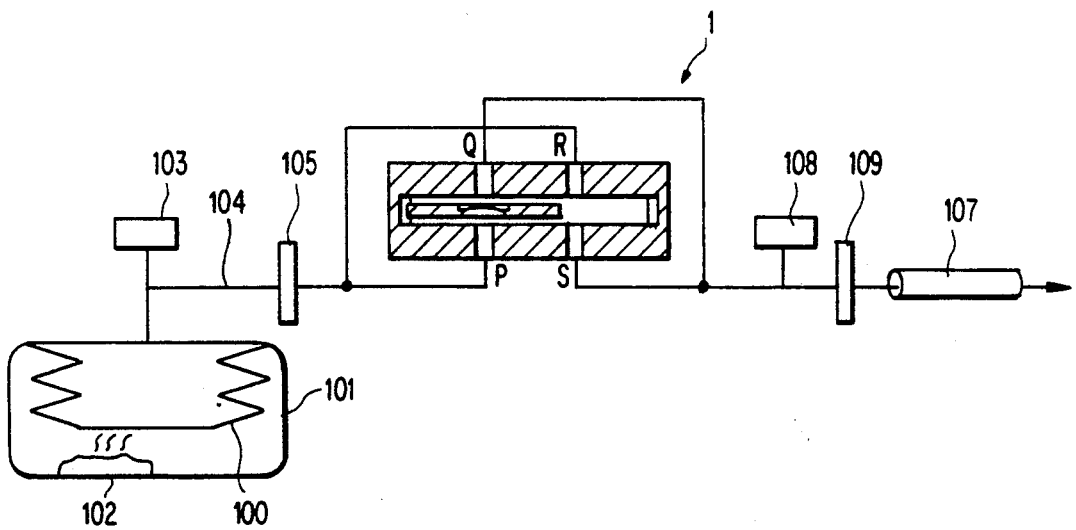
FIGS. 8a, 8b, 8c and 8d illustrate fourth and fifth preferred embodiments of this invention employing a planar configuration with diaphragm-type shuttles.

Referring now to FIG. 8a, a fourth preferred embodiment of this invention is depicted in schematic form. Here the passive shuttle metering device 1 is represented in a planar slider configuration similar to the embodiment of FIGS. 2a and 2b except that the porting of the flow system has been altered to form two high pressure channels "P" and "R" geometrically opposed to two low pressure channels "Q" and "S", respectively. As will be detailed herein, the slider 3 has been altered to provide a shuttle component 4 whose direction is now orthogonal to the motion of the slider.

Figure 8B:
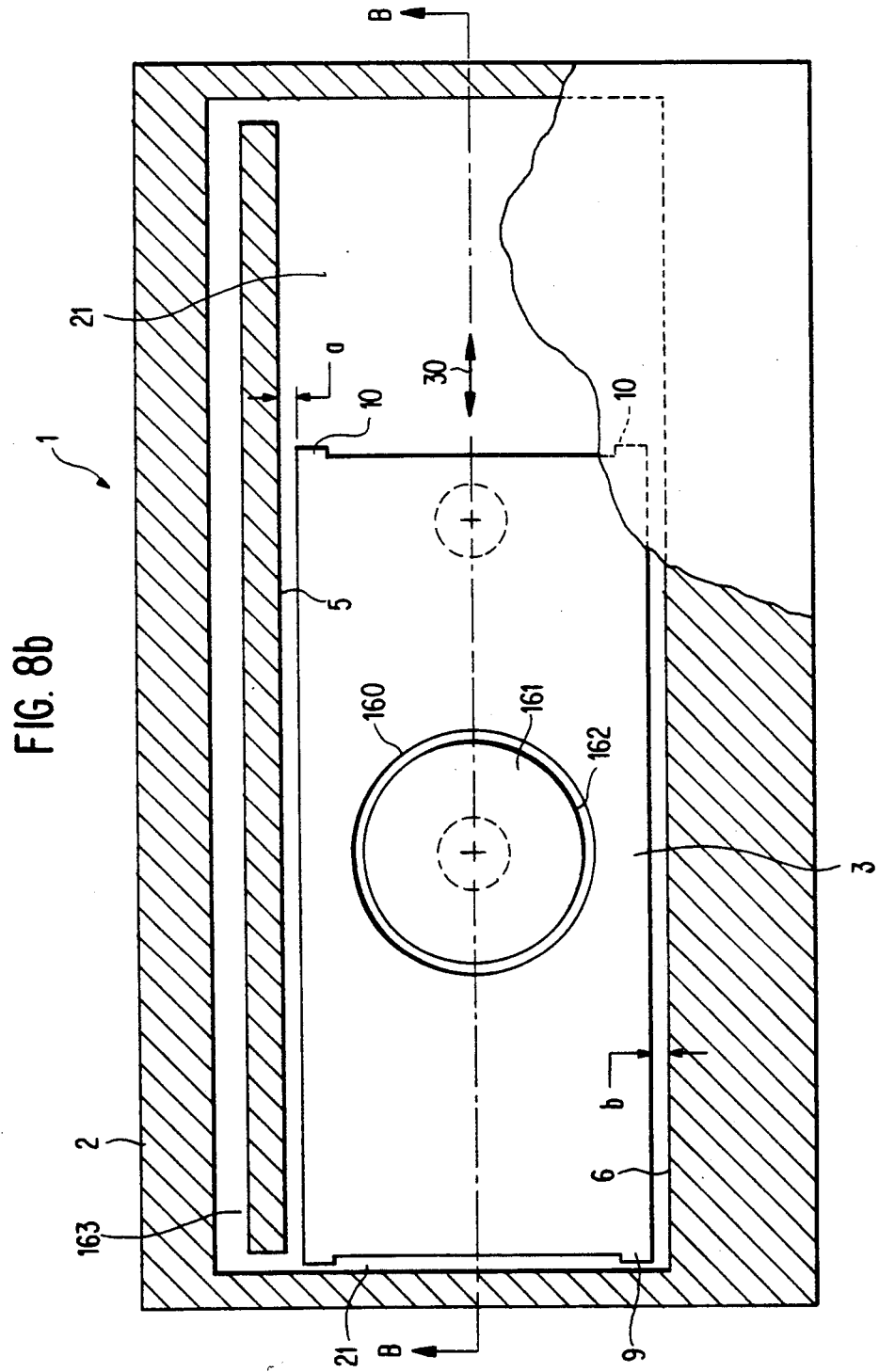
Figure 8C:
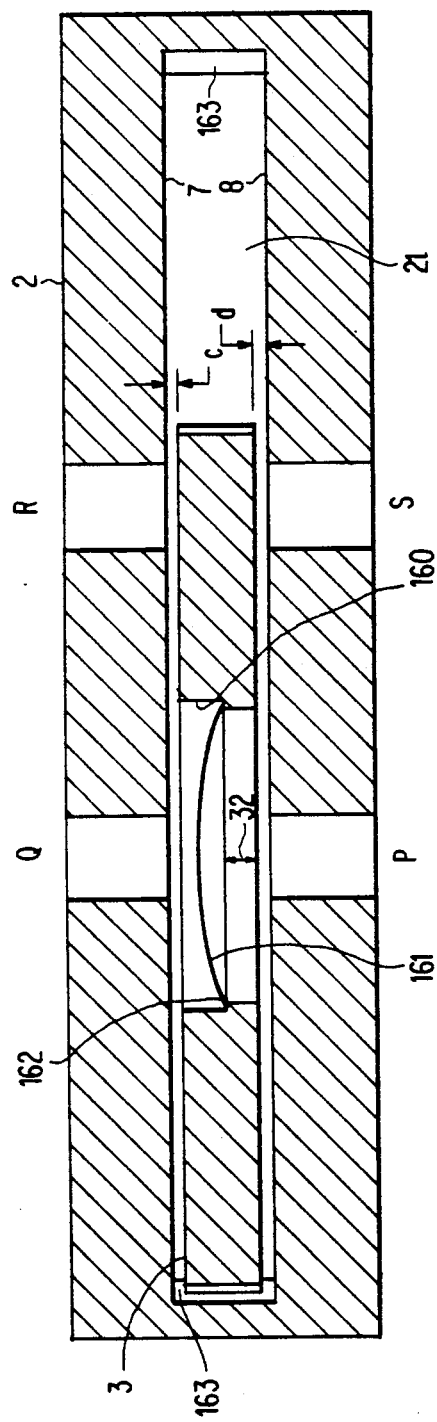

Referring now to plan view FIG. 8b and cross sectional view FIG. 8c, where like elements to FIGS. 2a and 2b are given like numbers, a fourth preferred embodiment is shown which is functionally similar to that of FIG. 2a, in that the housing 2 constrains a movable slider 3 along bearing surfaces 5, 6, 7 and 8. However, centrally fixed within the slider 3 is a perpendicular cylindrical bore 160 hermetically joined to flexible diaphragm 161 through sealing joint 162.

In the operation of this embodiment, as the slider 3 is moved back and forth in the directions indicated by the double-sided arrow 30, shuttle diaphragm 161 is caused to be in alternate fluid communication with high and low pressure channel pairs P/Q, and R/S. The operation is similar to that in FIG. 2a and FIG. 2b except that the porting is adapted to a direction of shuttle movement perpendicular to that shown in the first embodiment. This movement is represented in FIG. 8c by the double-sided arrow 32. For instance, referring to FIG. 8c, the flexible diaphragm 161 is shown bowed upwards in response to the high pressure of channel P with respect to the low pressure of channel Q; this is the resting state of the diaphragm 161 in the position of the slider 3 shown in FIG. 8c. In a fashion similar to other embodiments, a fixed quantity of fluid is displaced out of channel Q as high pressure from channel P forces fluid upwards into the diaphragm 161. The tension within the shuttle diaphragm 161 prevents fluid from displacing more than the calibrated volume, resulting in a flowrate waveform similar to FIG. 4a through catheter 107.

When a new pulse of fluid is required, the slider 3 of FIG. 8c is moved towards the right (driver and linkage not shown), recirculating fluid in sealed housing 2 from the righthand side of fluid cavity 21 through bypass channel 163 to the lefthand side of the slider 3 until the slider contacts the righthand wall of the housing 2 on limit tabs 10. The top of shuttle diaphragm 161, formerly in contact with low pressure channel Q is now exposed to high pressure fluid in channel R, while simultaneously, the fluid volume below diaphragm 161 is exposed to low pressure channel S. This reversal of pressure drives the shuttle diaphragm 161 downward, repeating displacement of a fixed pulse volume into the low pressure channel S, through the particulate filter 109 and out the catheter 107. This action will produce an output equivalent to that of FIG. 4c. The cycle will be completed when another flow pulse is required and the slider 3 is driven to its original position as indicated in FIG. 8c.

Figure 8D:
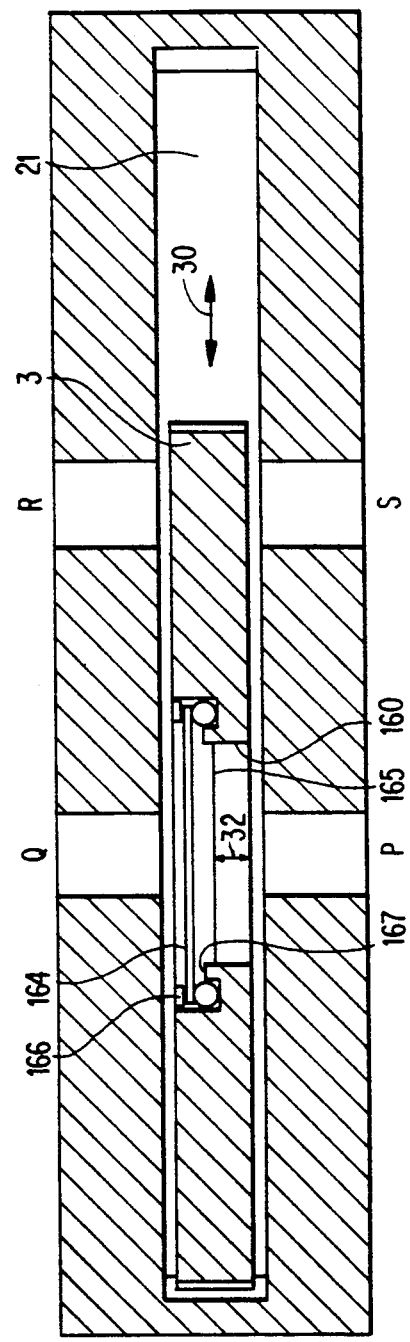

Finally, referring to FIG. 8d, a modification of the preferred embodiment to the shuttle diaphragm of FIGS. 8b and 8c is shown. Here, a shuttle plate 164 is shown positioned within perpendicular bore 160 in slider 3. The circular shuttle plate 164 is held against O-ring face seal 165 by annular retainer 166 which is securely fastened to the slider 3 through welding, gluing or the like. Annular rim 167 constrains the o-ring 165 and acts as a limit stop to control the downward motion of the shuttle plate 164 as will be described herein.

The shuttle plate 164 compressed against the O-ring 165 forms a flexible fluid tight seal between high pressure channel P and low pressure channel Q. However, the compression force on the O-ring 165 used to generate the fluid seal is much less than the force created by the differential pressure across the shuttle plate 164 and therefore, the shuttle plate 164 will be free to move up and down in the direction shown by the double-sided arrow 32 in response to the pressure differences between channels P and Q and channels R and S. This travel of the shuttle plate 164 is controlled by the positions of the retainer 166 and the limit stop 167. Therefore, in response to the cyclic motion of the mechanical slider 3 as it moves between the pressure channel pairs P/Q and R/S (arrow 30), fixed, repeatable pulses of fluid will be ejected from the outlet catheter 107 as in the other shuttle embodiments.

While a number of preferred embodiments have been described herein, it will be appreciated by those of working skill that this invention is not limited thereto. Other embodiments can be used consistent with the scope of the disclosure herein.

Having described our invention, we claim:

1. An implantable delivery device comprising;
a source of fluid under pressure,
a conduit for fluid delivery,
a metering element receiving fluid from said fluid source and delivering discrete fluid pulses to said conduit, said metering element comprising a housing having an inlet in fluid communication with said source, an outlet in fluid communication with said conduit and a cavity in said housing in fluid communication with said inlet and outlet, first movable means mounted in said cavity for movement relative to said inlet and said outlet and second movable means retained by said first movable means and movable relative to said outlet, said second movable means responsive to a pressure difference in said cavity for expelling fluid from said cavity into said outlet, and means to move said first movable means.

2. The implantable device of claim 1 wherein said first movable means comprises a slider mounted in said housing, said slider having a recess with a predetermined volume and said second movable means comprises a shuttle mounted in said recess and movable responsive to said fluid pressure difference in said recess.

3. The implantable device of claim 2 wherein said housing comprises guide means for constraining movement of said slider and defining a path around said slider for fluid to pass from said inlet to said outlet at a predetermined rate.

4. The implantable device of claim 1 further comprising means for controlling said means to move, wherein fluid pulses are delivered from said metering element at a predetermined rate.

5. The implantable device of claim 1 wherein said first movable means comprises cylinder means mounted in said cavity, a yoke holding said cylinder means, said means to move moving said yoke to change the position of said cylinder means in a cavity and said second movable means comprises a cylindrical shuttle mounted in said cavity in axial alignment with said cylinder means.

6. The implantable device of claim 5 wherein said cylinder means comprises a pair of separated cylindrical elements and said cylindrical shuttle is aligned with said separated cylindrical elements.

7. The implantable device of claim 6 further comprising a second outlet, said fluid inlet positioned between said outlets.

8. The implantable device of claim 1 wherein said first movable means comprises a cylindrical member rotatable in said housing, said cylindrical member having a bore positioned perpendicular to the axis of rotation of said cylindrical member, and wherein said second movable means comprises a shuttle positioned in said bore.

9. The implantable device of claim 8 wherein said housing has said inlet and outlet on opposite sides thereof and said cylindrical member is rotatable to align said bore with said inlet and said outlet.

10. The implantable device of claim 1, wherein said first movable means comprises a slider mounted in said housing, said slider having a recess with a predetermined volume and said second movable means comprises a diaphragm deflectable relative to said inlet and said outlet.

11. The implantable device of claim 10 further comprising a second inlet and a second outlet in said housing, said first inlet positioned opposite said second outlet, and said second inlet positioned opposite said first outlet, wherein movement of said slider positions said diaphragm alternately between an inlet and outlet for simultaneous fluid delivery and refill.

12. An implantable delivery device comprising;
a source of fluid under pressure;
a conduit for fluid delivery;
a metering element receiving fluid from said fluid source and delivering discrete fluid pulses to said conduit;
said metering element comprising a housing having an inlet in fluid communication with said source, an outlet in fluid communication with said conduit and a cavity in said housing in fluid communication with said inlet and outlet, first driven movable means mounted in said cavity adjacent said inlet and outlet, second movable means carried by said first movable means and movable relative to said outlet as a function of a pressure differential across said second means, and means to move said first movable means to positions opening and blocking said outlet, wherein by positioning said second means fluid from said source is admitted into said cavity and by subsequent movement of said second movable means relative to said outlet, a pulse of fluid is delivered into said conduit.

13. The implantable device of claim 12, wherein said first movable means comprises a slider mounted in said housing, said slider having a recess and said second movable means comprises a flat shuttle mounted in said recess and movable responsive to a fluid pressure differential in said recess.

14. The implantable device of claim 13, wherein said housing comprises guide means for constraining movement of said slider and defining a path around said slider for fluid to pass from said inlet to said outlet at a predetermined rate.

15. The implantable device of claim 12 further comprising means for controlling said means to move, wherein fluid pulses are delivered from said metering element at a predetermined rate.

16. The implantable device of claim 12, wherein said first movable means comprises a segmented cylinder mounted in said cavity, a yoke holding said segmented cylinder, said means to move attached to said yoke to change the position of said segmented cylinder in said cavity and said second movable means comprises a cylindrical shuttle mounted in said cavity in axial alignment with said segmented cylinder and between segments thereof.

17. The implantable device of claim 16, wherein said cylinder comprises a pair of axially aligned cylindrical segments and said cylindrical shuttle is aligned with said cylindrical segments.

18. The implantable device of claim 17 further comprising a second outlet, said fluid inlet positioned between said outlets.

19. The implantable device of claim 12, wherein said first movable means comprises a cylindrical member rotatable in said housing, said cylindrical member having a bore positioned perpendicular to the axis of rotation of said cylindrical member, and wherein said second movable means comprises a shuttle positioned in said bore.

20. The implantable device of claim 19, wherein said housing has said inlet and outlet on opposite sides thereof and said cylindrical member is rotatable to align said bore with said inlet and said outlet.

21. The implantable device of claim 12, wherein said first movable means comprises a slider mounted in said housing, said slider having a recess with a predetermined volume and said second movable means comprises a diaphragm deflectable relative to said inlet and said outlet.

22. The implantable device of claim 21 further comprising a second inlet and a second outlet in said housing, said first inlet positioned opposite said second outlet, and said second inlet positioned opposite said first outlet, wherein movement of said slider positions said diaphragm alternately between an inlet and outlet for simultaneous fluid delivery and refill.

23. The implantable device of claim 12, wherein said means to move said first movable means comprises a magnet positioned in said housing and a shape memory alloy coupled to said magnet to move it and thereby drive said first movable means.

* * * * *